United States Patent [19]

Komlos

[11] Patent Number: 4,723,625

[45] Date of Patent: Feb. 9, 1988

[54] SOBRIETY TESTER

[75] Inventor: Steven M. Komlos, Paradise Valley, Ariz.

[73] Assignee: Susan Komlos, Paradise Valley, Ariz.

[21] Appl. No.: 809,433

[22] Filed: Dec. 16, 1985

[51] Int. Cl.$^4$ .............................................. B60K 28/00
[52] U.S. Cl. ..................................... 180/272; 128/745; 340/576
[58] Field of Search ....................... 180/272, 271, 287; 340/53, 576; 123/198 DC; 128/745

[56] References Cited

U.S. PATENT DOCUMENTS

| 3,698,385 | 10/1972 | Low et al. | 128/745 |
|---|---|---|---|
| 3,707,710 | 12/1972 | Adler et al. | 128/745 |
| 3,755,776 | 8/1983 | Kotras | 180/272 |
| 3,886,540 | 5/1975 | Sussman et al. | 180/272 |
| 3,913,086 | 10/1975 | Adler et al. | 180/272 |
| 4,166,452 | 9/1979 | Generales, Jr. | 128/745 |
| 4,169,592 | 10/1979 | Hall | 128/745 |

Primary Examiner—John J. Love
Assistant Examiner—Kenneth R. Rice
Attorney, Agent, or Firm—Cahill, Sutton & Thomas

[57] ABSTRACT

A sobriety testing device subjects the operator of a motor vehicle to a test before permitting the engine of the motor vehicle to be started, and prevents the engine from being started if the test reflects that the operator's reflexes are impaired. The sobriety testing device includes a hand-held unit having a base position button, as well as left and right test buttons. During testing, the left and right test buttons are randomly illuminated, and a determination is made of the reflex time required to move the operator's finger from the base position to the indicated test button and back to the base position. A base norm reflex time is recorded by the testing device representing the operator's reflex time when free of any physical or emotional impairment. The sobriety testing device compares the operator's current reflex time with the previously recorded base norm and disables the engine if the operator's performance is significantly below the base norm.

17 Claims, 8 Drawing Figures

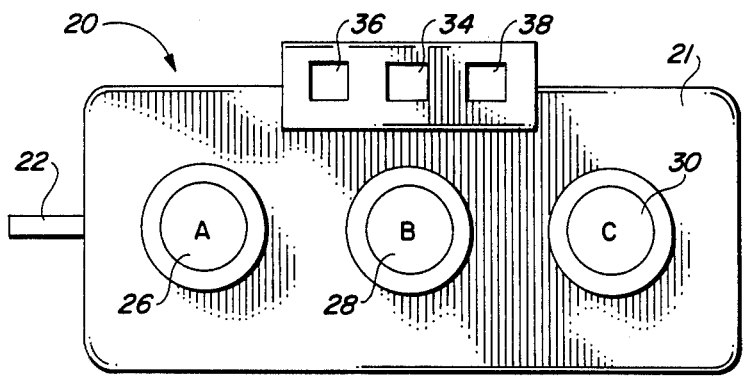
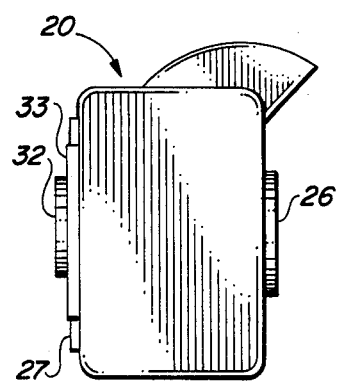
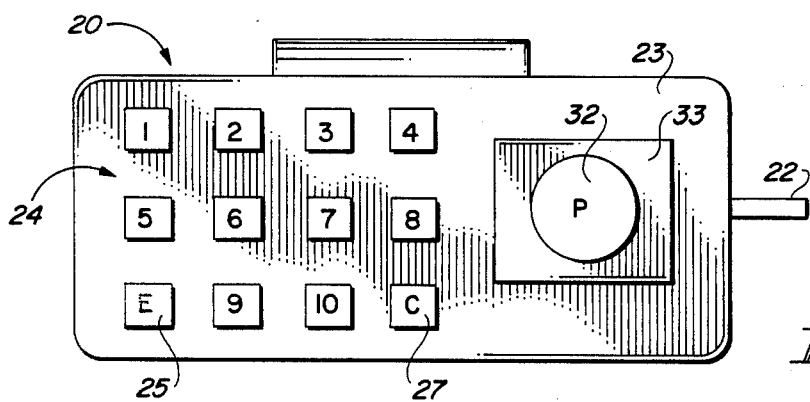
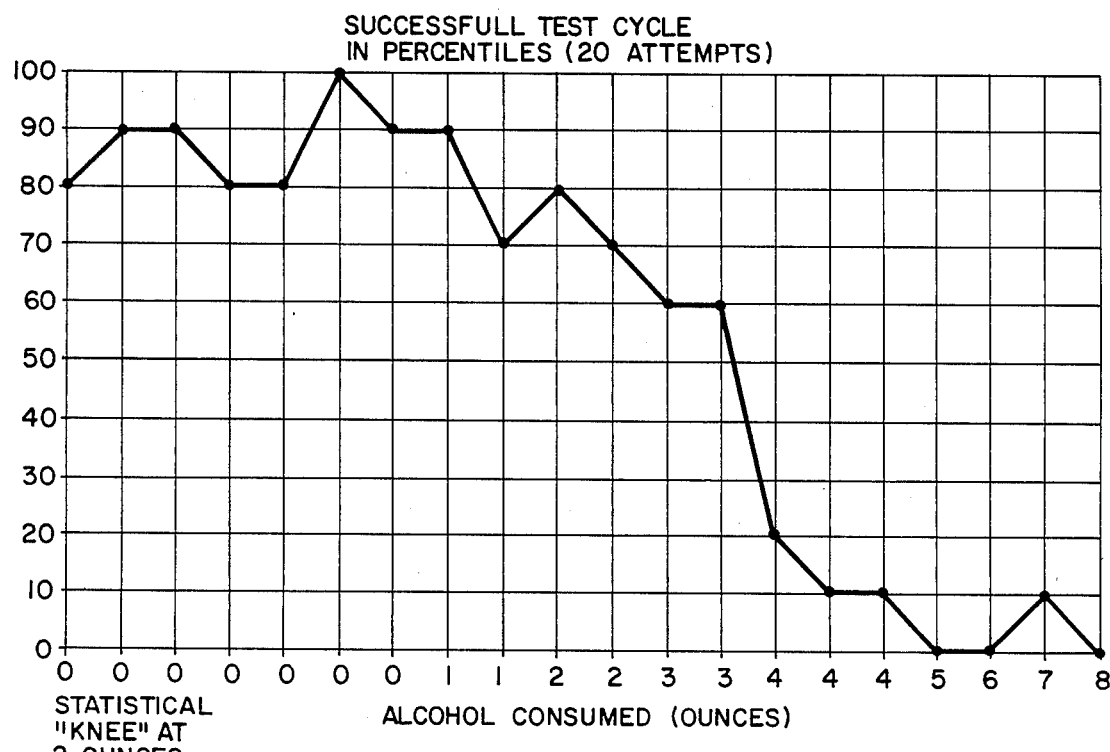

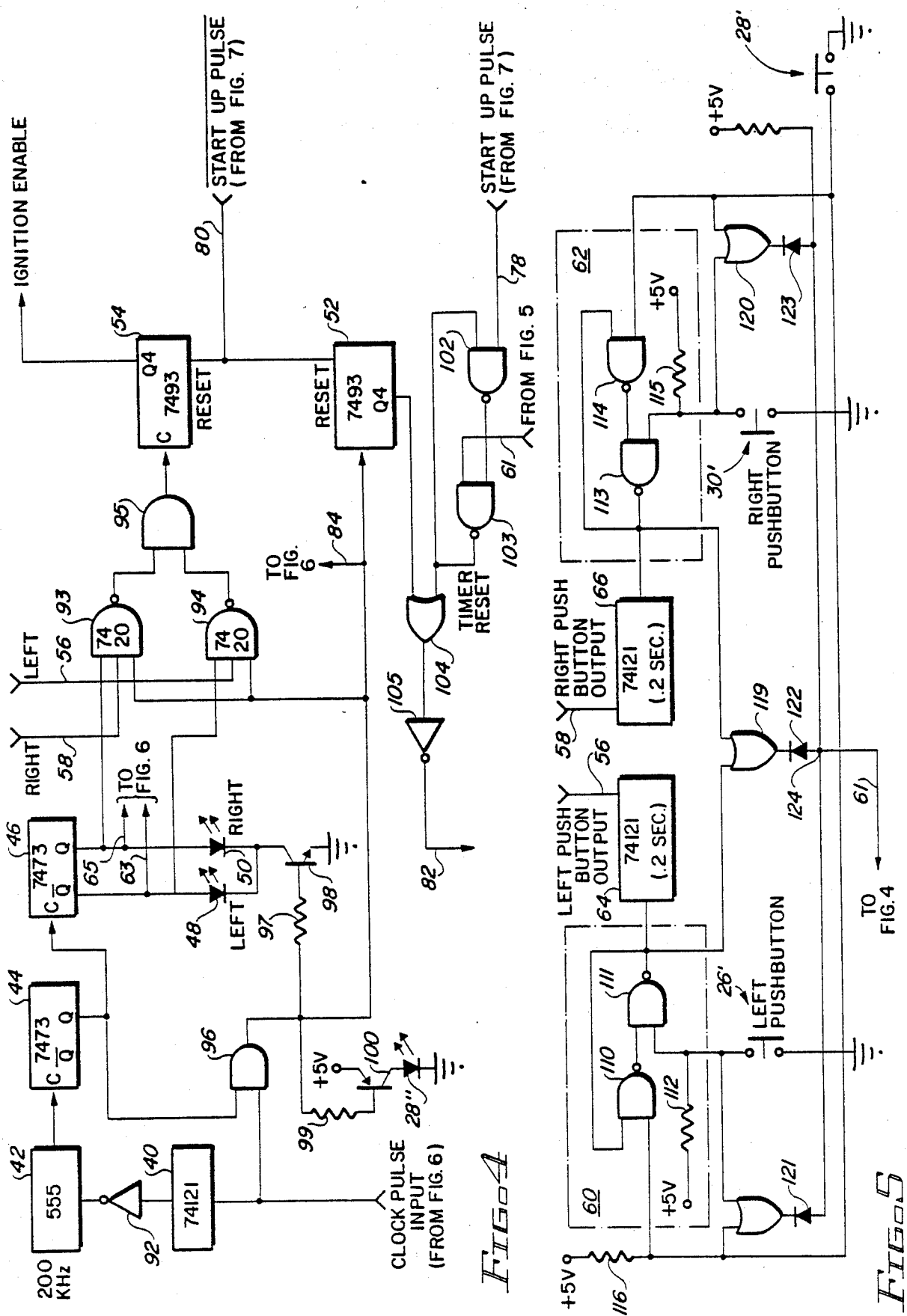

SOBRIETY TESTER

BACKGROUND OF THE INVENTION

1. Field of the Invention

This invention relates to apparatus used to prevent individuals who are reflex-impaired, due either to a lack of emotional capacity or due to intoxicating blood alcohol or drug levels, from operating a motor vehicle, and more particularly, to such an apparatus which circumvents the actual ability of a reflex-impaired driver to start the engine of his or her vehicle.

2. Description of the Prior Art

Prior art devices designed to prevent a person of diminished capacity from operating a motor vehicle are disclosed in U.S. Pat. Nos. 3,755,776, issued to Kotras; 3,886,540, issued to Sussman et al.; and 3,913,086, issued to Adler et al.

People drink alcoholic beverages, occasionally, to excess, and still attempt to drive their automobiles afterwards. Whether they simply do not recognize their impaired reflex abilities to do so safely or whether they feel the need to "get home" at all costs; the disastrous results are the same. It would be unlikely for inebriated individuals to acknowledge the risks that they are taking by attempting to drive while under the influence to not only themselves, but to those innocent individuals they are likely to meet, by sheer coincidence while on their way to their destination, in the course of their reflex-impaired operation of the vehicle.

Intoxicated drivers are only a partial cross-section of people who should not be operating a motor vehicle at any given time.

Included in this dangerous group are those individuals who are temporarily emotionally impaired since they are equally dangerous to the safety of the overall population. Some pertinent examples of emotionally impaired persons might be but are not limited to people in a high state of anger, whether they have just had a fight with a spouse or friend, young adults upset at their family and or world, individuals who are late to get somewhere and are overly anxious about it, individuals who might deem their necessity to be somewhere "now" as emergencies, and certainly not last or least, those who are experiencing real or imagined "medical emergencies".

Emotionally-impaired people, when tested, show a direct, predictable correlation between their reflex-impairment (their reflexes slow down and become erratic) and their emotional state at the time of testing. Reflex-impaired drivers include:

1-Those having drugs in their systems (whether prescribed by a doctor or simply "street drugs").

2-Those who have been prescribed medication by a doctor in order to bring their otherwise inadequate reflex systems up to a reasonable level of proficiency and have neglected or forgotten to take these medications;

3-Those individuals taking medically prescribed drugs which have been shown to cause a slowing down of the nervous systems ability to respond to outside stimuli either as a required result or as a side effect. An intoxicated, emotionally or otherwise "reflex-impaired" driver can with the use of the present invention, be identified and circumvented from operating his or her vehicle. It is also a concern to public safety that experienced drinkers, depending on the level of intoxication or impairment might be able to fake their condition long and well enough to get by the otherwise well meaning eyes of friends, bartenders and even policeman if the performance is acted out well enough. A serious social drinker, an alcoholic, a perpetual drug user or drug addict will surely have learned to act his way out to his car, past all the well meaning friends. The frightening end result to this scenario is the all to well recognized "fatality statistic".

SUMMARY OF THE INVENTION

The present invention can be generally describe as a device which makes unique use of electronics in determining a would-be driver's "reflex-alertness" and consequently makes use of this test data to compare it to the, medically expected, nuerological correlation of reflex deterioration upon intoxication, barbiturate use or emotional stress.

This reflex test makes possible the continuous, automated comparison, of an individuals reflex condition at the present time, with what has been tested and recorded previously (at a time when the would-be driver was free of alcohol, drugs and emotional stress) into electronic memory, as his or her "base-norm" reflex alertness (speed).

As used herein, the term "reflex-impaired" refers to any individual whose reflex response speeds, as tested by the present invention, grossly deviate, by being significantly slower or more erratic, from his or her previously tested "base-norm".

As used herein, the term "base-norm" refers to the speed with which the device disclosed herein has electronically tested the reflexes of the operator under normal conditions when the operator is in total control of his or her physical and emotional facilities, and is thus, the established, highest speed at which the operator can repeatedly and successfully operate the device disclosed herein. The base-norm is established when the device disclosed herein starts testing the driver at the slowest of its ten speeds. The response times are computed, and when they exceed a predetermined safety margin, the device automatically advances to its next faster speed. This procedure is repeated until the person being tested peaks out at their fastest, and yet still reliable and repeatable, speed (the "base-norm"). Testing has shown that six to twelve attempts are required for an individual to reach the base-norm (depending upon normal deviations in reflex speeds of individuals). The final speed setting of the person being tested is recorded into a memory, for future comparison. This final speed setting is the individual's base-norm speed.

As used herein, the term "speed" refers to the reflex time required by a particular driver to discern that one of two lights are illuminated, to make the proper identification (left or right), and finally to move his or her finger from a resting position button to a button corresponding to the light which they have perceived to be illuminated. They need to depress the illuminated button in as short a time as possible. This action is randomly and electronically repeated four times and constitutes one testing cycle. The speed at which the finger is returned to the resting button is also measured and taken into account for the final reflex analysis.

References are made herein to the requirement for the operator to operate the testing device reliably and repeatably. Improper operation of the test buttons, i.e., depressing any two buttons simultaneously, not releasing one button before depressing the other button, or totally missing the buttons, will be interpreted by the device disclosed herein in the same manner as having operated the test too slowly. Both mistaken operation, as well as delayed operation, will be interpreted as failures and result in the device disclosed herein judging the driver as being reflex-impaired.

It is imperative that the device disclosed herein determine the operator's base-norm speed while the individual is reflex-able, meaning that, at the time when the base-norm is automatically established by the present invention, that the tested individual's sensory and endocrine system is:

1. Free from even minute traces of alcohol;
2. Free of excess emotional stress and anxiety;
3. Free of non-prescription drugs, barbiturates or mood altering drugs;
4. Free of medically prescribed mediations which are labelled with warnings against use while operating a motorized vehicle (blood pressure, heart, and anti-depression medications, as an example); and
5. In a normal medical condition as assured by the proper and timely administration of all medically prescribed medications that are non-mood altering.

A person is deemed reflex-able by having met the above-mentioned five medical parameters during the approximately six to twelve times that he or she initially operates the device disclosed herein. This reflex-able speed is determined and recorded into a permanent memory immediately after the initial operation of the device by a driver following the installation of the device into a vehicle. It is this base-norm speed against which the reflex-impaired individual must compete, in future tests, in order to start his or her automobile.

The driver is deemed to reflex-impaired when he or she attempts to operate the present invention but is unable to do so as consistently, and at such a speed, as was accomplished by the user during the previously-described base-norm.

The appropriate state agency, having granted the individual the privilege of driving, as witnessed by the issuance of a drivers licence, has already deemed through involved testing procedures that the individual is indeed capable of operating a vehicle safely when the individual is in a normal nuerological state. The present invention helps to avoid the necessity for a police officer, friend, or bartender to make a spot judgment as to the driver's level of intoxication, use of drugs, and/or emotional condition at the time that the driver attempts to operate his or her automobile.

BRIEF DESCRIPTION OF THE DRAWINGS

FIG. 1 is a top view of the front panel of the hand-held portion of one embodiment of the present invention.

FIG. 2 is a top view of the rear panel of the hand-held portion shown in FIG. 1.

FIG. 3 is a side view of the hand-held portion shown in FIGS. 1 and 2.

FIG. 4 is an electronic circuit schematic showing a random generator circuit used in the disclosed embodiment of the present invention.

FIG. 5 is an electronic circuit schematic showing a push-button interlock and input conditioning circuit for the disclosed embodiment of the present invention.

FIG. 8 is a graph showing an example of a reflexable operator taking the test performed by the present invention, and further showing a sharp, distinct and abrupt statistical knee drop-off in performance upon the operator becoming reflex-impaired.

DETAILED DESCRIPTION OF THE PREFERRED EMBODIMENT

Figure 6:
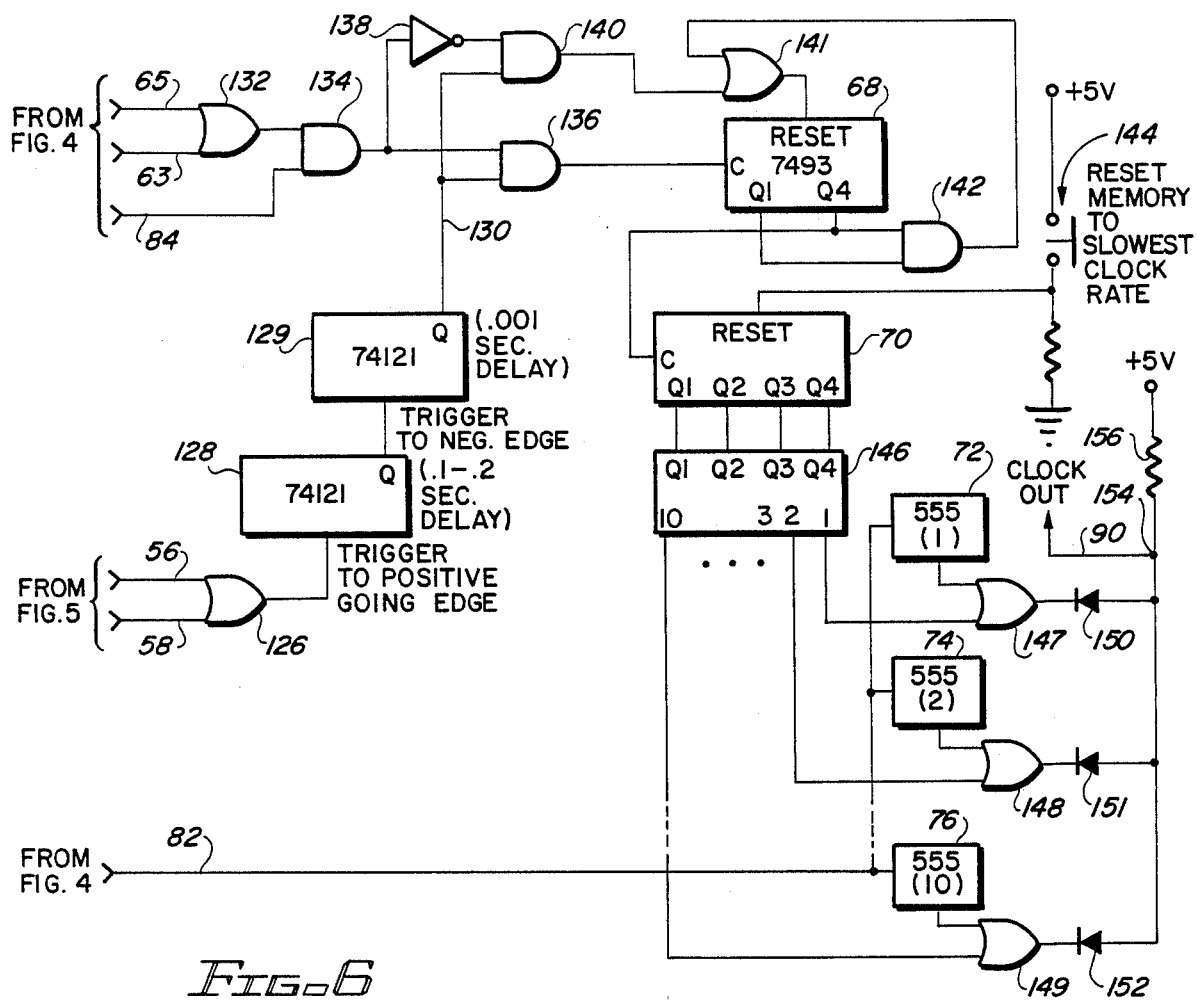
FIG. 6 is an electronic circuit schematic showing an automatic speed adjust circuit used in the disclosed embodiment of the present invention.

As shown in FIGS. 1–3, the actual operator-interactive testing portion of the sobriety testing device is a hand held unit 20 (Aprox 2.5"×2"×5") and is thus mounted for driver convenience via a conventional quick release bracket, (not shown) inside the driver compartment of the automobile. The actual electronic bulk of the unit is mounted under the dash and the two are connected via a standard coiled wire 22.

Wiring of the sobriety testing apparatus to the ignition system of a vehicle is accomplished with an interruption of the two ignition switch leads (not shown) prior to their going to the COIL and STARTER. An additional interrupt must be located and wired between the horn switch and the horn itself. These are suggested placements of the interrupt, and the proper use of the sobriety testing device is certainly not limited to these methods. Installation will vary with the particular automobile. The important factor is to interrupt these wires in a neat and non obtrusive manner, the intent being to make "hot wiring" of the automobile as close to impossible as it is as originally designed by the auto manufacturer.

Once the "interrupt" wiring is properly completed, it is impossible to engage the starter of the automobile without the would-be-driver having to successfully deal with the sobriety testing device.

Before proceeding further into the description of the specific operation of the sobriety testing device, it may be helpful to review the basic principle of operation upon which the sobriety testing device disclosed herein is based. The sobriety testing device constitutes an electronic method by which operators are prevented from operating, or even starting, their cars unless they are reflex-able to do so. If, for whatever reason, an operator is reflex-impaired, the sobriety testing device will prevent the operator from being able to start his or her car. The sobriety testing device is designed to measure the reflexes of the operator before permitting the operator to start the vehicle. If the potential driver's reflexes are not operating at a reasonably high level of proficiency, then the sobriety testing device will not allow the driver to start the vehicle. This judgment of reflex proficiency is a direct computerized comparison/correlation to the driver's own base-norm speed. As stated earlier, the established base-norm was recorded at a time when the driver's reflexes were at a premium, i.e., the driver was cold sober, not emotionally upset, nor otherwise emotionally or physically impaired, and hence in total control of his or her reflexes.

When testing the potential driver, the sobriety testing device will detect any significant deviation (reflex-impairment) from the above-mentioned high level of reflex proficiency, during the base-norm period, and prevent the driver from starting the automobile if such a deviation is detected.

The sobriety testing device analyzes the reflex ability and reflex accuracy of a potential driver every time that the driver attempts to start his or her automobile. This analysis will be automatically and constantly compared to the driver's previously determined base-norm or best reflex response. If the presently tested reflex response is significantly slower or less consistant than the base-norm, then the sobriety testing device will prevent the automobile from being started. Because the sobriety testing device is completely electronic, and responds only to the measured reflexes of the driver, it cannot be fooled by the sober pretense of a reflex-impaired driver. The sobriety testing device judges an individual's ability to safely operate a complex motor vehicle strictly by detecting reflex-impairment, whether due to excessive use of alcohol, drug abuse, emotional anxiety, excessive age, or failure to take prescribed medications.

The successful operation of the sobriety testing device during normal, every day use requires a total of only 10 to 12 seconds of the driver's time, and only 4 to 7 seconds of serious, undivided attention. Obviously, the safe operation of an automobile requires more intense and longer periods of attention, a higher degree of alertness, and in general a higher state of reflexability, than that required to operate the electronic sobriety testing device. If an individual cannot successfully operate the electronic sobriety testing device, he or she could not possibly operate an automobile in a safe and prudent manner. Having failed the sobriety testing device test, the individual should not be allowed to operate the motor vehicle until such time that he or she has recovered sufficiently from their temporary reflex-impairment.

With the above understanding of the basic principles of the invention in mind, a description of the manner in which the sobriety testing device is used will now be set forth.

1-Upon entering the vehicle the driver engages the ignition key to "on" (labeled "accessory" in most automobiles) in the normal manner. This action will enable only the touch tone pad 24 of hand held unit 20 to become electronicly armed. Any attempt to engage the coil and starter in order to gain "ignition" will be unsuccessful at this time. The driver will experience the very same response as though his car battery was dead or his starter motor had failed.

2-The driver must enter his or her pre-selected 4 digit code (personal identification number) upon key pad 24. By identifying himself, the driver has automatically selected one of four memories previously chosen by the particular driver as his personal identification number (there are four memories in the unit in order to accommodate multi-user automobiles). This memory will correlate the identified driver with his previously tested reflex "base-norm" and set the speed of the sobriety testing device automatically.

3-Within a two to four second time delay, the ready light (yellow) will activate on the device, alerting the user of the imminent start of the "reflex-impairment" test.

4-When the yellow (ready) light 34 (FIG. 1; 34 in FIG. 7) goes out, the driver must stay alert, since he has now begun the actual testing procedure.

5-The actual testing hardware is comprised of; three rear illuminated momentary contact switches 26, 28 and 30 (two red and one green). These switches will be mounted in a linear configuration, one green switch 28 in the center of the linear arrangement and the other two red switches 26 and 30 symmetrically disposed on the left and right hand corners of the linear configuration, as shown in FIG. 1. The center switch (green) will be the "base" position for the hand. This "base" switch 28 is illuminated for the duration of the test. The driver must maintain constant pressure on this switch at all times during the test with the brief exception of the times when he has committed himself to, and is in the process of, depressing one or the other of the two red switches 26 and 30. These other two switches 26 and 30 (left and right RED) will not be illuminated at the onset of the test but will begin their randomly activated illumination cycles after the driver has armed the sobriety testing device and conveyed his willingness to be tested by actively depressing the base switch 28 (center-green).

This on and off illumination of switches (always one of the two possibilities at any one time) is extremely random as activated by the electronic brain of the sobriety testing device. It is humanly impossible to successfully and repeatedly out-guess the sequence of these switches.

The left or right (red) switches 26 and 30 will illuminate for a total of four random cycles, and the driver must successfully identify the correct illuminated switch and depress that switch accurately while it is still illuminated. He must then revert back to the "base" switch 28 as quickly and as accurately as his reflexes permit.

6-If he has been successful in depressing the proper switch and reverting back to "base" prior to the continuation of the sequence of lights and repeating this action four out of four attempts (100%) with speeds that fall within the acceptable range (acceptable range="base-norm"+safety margin of 0.132 seconds) as automatically compared to his previously tested "base-norm", then he has successfully passed his "test" and is deemed to be "reflex-able". The green light 36 shown in FIG. 1 will illuminate on the unit asserting that the ignition sequence has become armed. The driver should engage his ignition switch to the "starter" position at which time the automobile engine will commence normal operation.

7-If the red light 38 shown in FIG. 1 illuminates after the driver has attempted to keep up with the random illumination of the two side switches, 26 and 30 then he has been judged "reflex-impaired" at this time.

Having failed the reflex test on his first attempt, the driver may re-activate the entire sequence by turning the ignition key to off and back to "on". The driver should attempt the above described sequence steps 2. through 6. at this time, since he is allowed a second and final "pre-penalty" test. This buffer is needed since it is possible to accidentally spoil the testing procedure one time for reasons other than "reflex-impairment". The mathematical probability of missing twice in succession is too remote to consider a coincidence.

Failure of the second test will result in a "reflex-impaired" interpretation by the sobriety testing device and an automatically escalating time penalty will be electronicaly and automatically enacted from this point on, until such time that the test is eventually (successfully) completed by the would-be driver.

| TEST ATTEMPT Number of "test failures" | PENALTY Time delay prior to ability to re-test |
|---|---|
| First | None |
| Second | None |

| TEST ATTEMPT<br>Number of "test failures" | PENALTY<br>Time delay prior to<br>ability to re-test |
|---|---|
| Third | 15 Minutes |
| Fourth | None |
| Fifth | 30 Minutes |
| Sixth | None |
| Seventh | 60 Minutes |
| Eight | None |
| Ninth | 60 Minutes |
| Tenth | None |

Any and all further attempts to "test" after the tenth successive "failure to pass" will continue to be penalized at 60 minutes for every two attempts. This sequence of penalties will continue indefinitely until a "pass" is registered (even if it takes until the next sobering morning).

EMERGENCY PROCEDURES

The present invention recognizes the possibility of this device getting in the way of a quick, panic type, escape from danger, since the driver would be less than likely to be able to operate the sobriety testing device properly if the driver were being accosted or in some other manner threatened with body harm. The minute, but still real possibility, for the need to escape immediately from a parking lot in such life threatening cases has prompted the inclusion of an emergency escape button.

The emergency escape button 32 can be depressed at any time without the sobriety testing device 20 having to be activated or the identification code having to be entered, and thus will make the sobriety testing device an attack deterrent alarm. The arming of this button deactivates the complete sobriety tester device while simultaneously and automatically sounding the automobile horn. The horn can be silenced only upon the ignition becoming disarmed, by the removal of the key. Turning the ignition off will re-set the sobriety testing device to sequence steps 1 through 5 as though the emergency escape button 32 had not been activated, allowing the operator to encode his or her identification number and take the sobriety test . . . when safe to do so. The emergency button has no limits on its use nor time penalties of any sort. The intent is to call attention to an emergency threat to life and limb while allowing the use of the automobile for the driver's escape. An automobile being driven with its horn blaring is going to attract the attention of police officers as well as well meaning passersby which is genuinely desired in the case of a real life threat. If the driver were intoxicated or otherwise reflex-impaired, he would be foolish to attempt to by-pass the sobriety testing device and start his car by the use of the emergency escape button since the last thing he wants is a blaring horn which would attract attention to his intoxicated condition.

It is believed that the deterrent of attracting attention via the activation of the vehicle horn will keep the user honest and prudent in the unnecessary or flagrant use of emergency escape button 32.

As an added advantage and incentive for the installation of the sobriety testing device device, said automobile, properly equipped, will be protected against theft or unauthorized use since the would be burglar would need to know the operators identification code and the rules of the sobriety testing device in order to gain entry to the ignition system of the automobile. Therefore just being able to enter the automobile or getting possession of the ignition key will no longer be enough to complete the theft of the car.

Referring to FIG. 1, the preferred embodiment of the present invention includes a number of below-described features visible upon the front face 21 of hand-held unit 20 as follows:

Yellow LED light 34 becomes active upon the operator arming the ignition switch in the automobile. Yellow light 34 signals the readiness of the sobriety testing device to begin the test.

Base testing switch 28 (B) illuminated in green, will be the base or resting position for the hand. This base switch is illuminated for the duration of the test. The driver must maintain contact (pressure) on this switch at all times during the test with the brief exception of the times when he has committed himself to, and is in the process of, depressing one or the other of two red switches 26 and 30 (A or C).

Random testing switches 26 and 30 (A+C) are in red. These switches will not be illuminated at the onset of the test but will begin their randomly activated illumination cycles, after the driver has armed the sobriety testing device (as indicated by the illumination of yellow light 34) and conveyed his willingness to be tested by actively depressing the base switch 28 (B).

This on and off illumination of switches 26 and 30 (always one of the two, A or C, at any one time) is extremely random as activated by the electronic brain of the sobriety testing device.

Pass of testing cycle indicator LED 36 (D) is green in color and is activated upon the operator having successfully depressed switches A, B, and C in the proper sequence and in the appropriate timing for a full cycle.

Failure of testing cycle indicator LED (38) is red in color and is activated upon the operator's failure to successfully depress switches A, B, and C in the proper sequence and in the appropriate timing for a full cycle.

referring now to FIG. 2, Escape Button 32 (P) is shown on the back side 23 of the hand-held unit 20. The emergency escape button can be depressed at any time without the sobriety testing device going through the testing cycle or having to be activated and thus will make the sobriety testing device an attack deterrent alarm. The arming of this button deactivates the complete sobriety testing device while simultaneously and automatically sounding the automobile horn and deterring intruders as well as drawing the attention of police officers. The horn can be silenced only upon the ignition becoming disarmed, by the removal of the key.

Still referring to FIG. 2 the 10 key operator identification key pad 24 (1 through 10) is shown. The additional 2 keys 25 and 27 are for "enter" and "cancel". The operator must turn the device over prior to testing and input his or her personal identification number in order to arm the testing portion of the device. Emergency escape button (P) is also shown, included is the safety accidental depress prevent cover 33, which needs to be raised in order to be able to "activate" the alarm.

The circuit schematic of FIG. 4 illustrates the circuitry used to randomly illuminate the left and right random testing switches 26 and 30 during test cycles. A clock signal pulse (generated by the circuitry shown in FIG. 6) is received by a trigger input of monostable multivibrator 40 which may be of the type commercially available from the Semiconductor Products Division of Motorola, Inc. in Phoenix, Ariz. under part No. MC74121P.

The 74121 multivibrator 40 puts out a 1/10 second pulse on the negative going edge of the clock signal which via inverter 92, enables the oscillator 42, which may be a timer of the type available from National Semiconductor of Santa Clara, Calif. under Model No. LM555. During the 0.1 second pulse, oscillator 40 puts out approximately 20,000 pulses. The output of oscillator 40 is coupled to the clock input of one of two series-connected flip-flops of the type commercially available from Motorola, Inc. under part No. MC7473P, designated within FIG. 4 by reference numerals 44 and 46. Because oscillator 40 is unable to put out exactly the same number of pulses each time, the count of flip-flops 44 and 46 is reasonably random. During the logic high portion of the clock signal, depending on the count of the two flip-flops 44 and 46, one of the LED's 48 and 50 (buttons A or C) may or may not illuminate depending upon the state of flip-flop 44. Also shown in FIG. 4 are two 4-bit binary counters of the type commercially available from Motorola, Inc. under part No. MC7493P, identified in FIG. 4 by reference numerals 52 and 54. If an LED 48, 50 (A or C) illuminates, the bottom 7493 ripple counter 52 is advanced one count on the negative going edge of the clock signal. The top counter 54 is advanced by pressing the push button (electrically coupled to conductors 56, 58 in FIG. 4) associated with the lit LED during the time the LED is lit (the high portion of the clock signal). When the top counter 54 reaches a count of 4, the automobile ignition is enabled via output Q4 of counter 54. If the bottom counter 52 reaches count of 4 first, then the test is over and the ignition will NOT be enabled.

PUSH BUTTON INTERLOCKS AND INPUT CONDITIONING

Referring to FIG. 5, a pair of RS flip-flops 60 and 62 provide input conditioning for left push button 26' and right push button 30'. The RS flip-flops 60 and 62 are coupled to a pair of monostable multivibrators 64 and 66, respectively, of the type available from Motorola, Inc. as MC74121P, and trigger the pair of 74121's set so that their output pulse is shorter than ½ cycle of the clock signal. This means that the RS flip-flops 60 and 62 must be re-set by activating the Base button (C) 28' before another push button pulse (A or C) can be generated.

The remaining gates are present in order to prevent pushing two buttons (A, B or C) 26', 28', or 30' at the same time. Depressing two buttons simultaneously in any combination thus has the same effect as having reached a count of four on the bottom 7493 counter 52 of the random generator circuit shown in FIG. 4.

AUTOMATIC SPEED ADJUST

Referring now to FIG. 6, after any one of the buttons 26', 28' or 30' (shown in FIG. 5) (A, B, or C) is depressed, the automatic speed adjust circuitry shown in FIG. 6 waits a fixed length of time (approx. 0.1 second, as determined by monostable multivibrator 128) and generates a short window via the output Q of monostable multivibrator 129. If the either LED 48 or 50 (see FIG. 4) is still on during this window, then the top 7493 counter 68 is advanced one count. If neither LED is on during the window, then the top 7493 is re-set to zero. After 4 counts of the top 7493 counter 68, the bottom 7493 counter 70 is advanced one count, selecting the next highest speed. In the first prototype this was accomplished by using a 1 of 10 decoder 146 coupled to the 4-bit output of counter 70 for gating 10 separate oscillators (72, 74 . . . 76). Decoder 146 may be of the type commercially available from Motorola, Inc. as part No. MC7442P. A better version would be to use a voltage controlled oscillator, as the MC4024 commercially available from Motorola, Inc.; the same decoder 146 could select 10 different voltage divider networks. Since the MC4024 contains two oscillators, more than the 3 to 1 range of one oscillator could be achieved.

START UP GENERATOR

Figure 7:
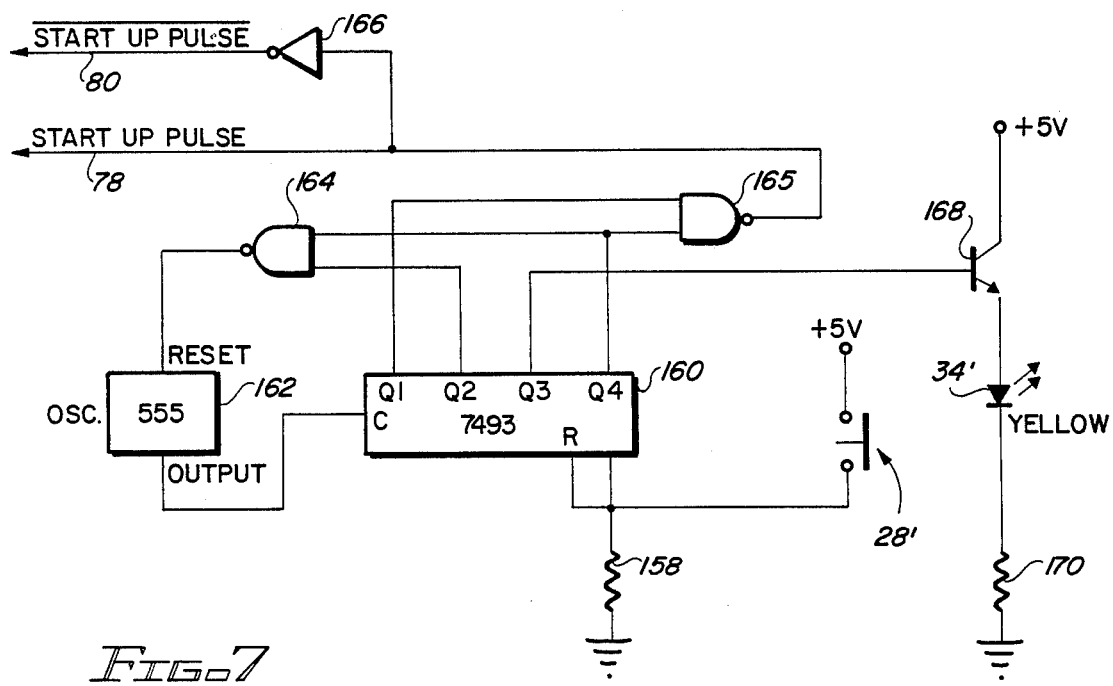
FIG. 7 is an electronic circuit schematic showing a start-up generator portion of the disclosed embodiment of the present invention.

Turning to FIG. 7, the start-up generator circuit shown therein generates the start-up pulses that reset the 7493 counters 52 and 54 of the Random Generator and the RS flip-flop (see gates 102 and 103 in FIG. 4) that is set by pushing two buttons inadvertently. It does this after lighting the yellow "test alert" light 34' (E) for a two second duration.

Throughout this specification, the terms "automobile", "driving", "safety on the roads", and other terms that connote the use of the sobriety testing device as a device that is intended strictly for automotive use, are used. Those skilled in the art will appreciate that the sobriety testing device disclosed herein is equally applicable to usage by operators of dangerous industrial-type machinery, i.e., road building equipment, cranes, earth moving devices, printing presses, compactors, cutters, military equipment, airplanes, helicopters or any other machinery and/or equipment wherein the reflex alertness of the operator is imperative to the safe and prudent operation of such equipment. In the non-automotive mode, the sobriety testing device could have as many as 64 separate identification memory codes, in order to allow multiple operator use.

The foregoing description is included to illustrate the preferred embodiment and is not meant to limit the scope of the invention. The scope of the invention is to be limited only by the following claims. From the foregoing description, many variations will be apparent to one skilled in the art that would yet be encompassed by the spirit and scope of the invention.

What is claimed is:

1. Apparatus for testing the reflexes of a subject comprising:
   a. first pressure sensing means for providing a first signal when pressure is applied thereto by said subject;
   b. second pressure sensing means for providing a second signal when pressure is applied thereto by said subject;
   c. third pressure sensing means for providing a third signal when pressure is applied thereto by said subject;
   d. second indicator means associated with said second pressure sensing means for specifying to said subject said second pressure sensing means;
   e. third indicator means associated with said third pressure sensing means for specifying to said subject said third pressure sensing means;
   f. specification means for activating one of said second and said third indicator means; and
   g. measurement means for determining a response of said subject to an indicator means selection by said specification means, said subject applying pressure to an associated pressure sensing means in response to activiation of one of said indicator means, said measurement means determining a reflex time required by said subject to remove pressure from said first pressure sensing means, to apply pressure to a pressure sensing means determined by said specification means and to reapply pressure to said first pressure sensing means.

2. The reflex testing apparatus of claim 1 wherein a plurality of reflex times are determined.

3. The reflex testing apparatus of claim 2 further including comparison means for comparing said plurality of reflex times to a predetermined quantity.

4. The reflex testing apparatus of claim 3 further including means for activating an associated system when said plurality of reflex times have a predetermined relationship with said predetermined quantity.

5. The reflex testing apparatus of claim 4 further including a fourth pressure sensitive means, said fourth sensing means activating said associated system and a signal device in response to preselected activity by said subject.

6. The reflex testing apparatus of claim 3 further including delay means for permitting determination of a next plurality of reflex times after a preselected period of time when said comparison means determines that a previous plurality of reflex times does not have a predetermined relationship with said predetermined quantity, said preselected time being a function of a number times said predetermined relationship is determined not to exist.

7. Apparatus for testing the reflexes of a subject comprising:
   a. first pressure sensing means for providing a first signal when pressure is applied thereto by said subject;
   b. second pressure sensing means for providing a second signal when pressure is applied thereto by said subject;
   c. third pressure sensing means for providing a third signal when pressure is applied thereto by said subject;
   d. second indicator means associated with said second pressure sensing means for specifying to said subject said second pressure sensing means;
   e. third indicator means associated with said third pressure sensing means for specifying to said subject said third pressure sensing means;
   f. specification means for activating one of said second and said third indicator means;
   g. measurement means for determining a response of said subject to an indicator means selection by said specification means, said subject applying pressure to an associated pressure sensing means in response to activation of one of said indicator means, said measurement means determining a reflex time required by said subject to remove pressure from said first pressure sensing means, to apply pressure to a pressure sensing means determined by said specification means and to reapply pressure to said first pressure sensing means, said measurement means determining a plurality of such reflex times; and
   h. comparison means for comparing said plurality of reflex times to a predetermined quantity, said predetermined quantity being established by said reflex testing apparatus.

8. A method for testing reflexes of a person comprising the steps of:
   a. applying pressure to a first pressure sensing device;
   b. selecting one of a plurality of second pressure sensing devices;
   c. determining a reflex time between removal of pressure from said first pressure sensing device and reapplying pressure to said first pressure sensing device after applying pressure to said selected second pressure sensing device;
   d. determining a plurality of such reflex times; and
   e. comparing said plurality of reflex times with a preestablished quantity.

9. The method for testing reflexes of claim 8 further comprising the step of activating an associated system when said plurality of reflex times and said preestablished quantity have a preselected relationship.

10. A method for testing reflexes of a person comprising the steps of:
   a. applying pressure to a first pressure sensing device;
   b. selecting one of a plurality of second pressure sensing devices;
   c. determining a reflex time between removal of pressure from said first pressure sensing device and reapplying pressure to said first pressure sensing device after applying pressure to said selected second pressure sensing device;
   d. determining a plurality of such reflex times;
   e. comparing said plurality of reflex times with a preestablished quantity; and
   f. determining said preestablished quantity by initially performing steps a., b., c. and d. when said person is known to be free of any reflex impairment.

11. The method for testing reflexes of claim 10 further comprising the step of redetermining a plurality reflex times when said preselected relationship is not established.

12. The method for testing reflexes of claim 11 further comprising the step delaying said redetermining step by an interval related to the number times that said preestablished relationship has not been established.

13. The method of testing reflexes of claim 12 further comprising the step of activating said associated system without establishing said preestablished relationship, said activating step further activating a signaling device.

14. The method of testing reflexes of claim 12 further comprising the step of associating a preestablished quantity for each of a plurality of persons, said associated preestablished quantity being used in said comparing step.

15. The method of testing reflexes of claim 14 further comprising the step entering a code sequence prior to said reflex testing, said code sequence determining said preestablished quantity.

16. Apparatus for testing the reflexes of a subject comprising in combination:
   a. a plurality of pressure sensing means each providing a signal when pressure is applied thereto by said subject;
   b. indicator means associated with said plurality of pressure sensing means for specifying to said subject which of said plurality of pressure sensing means are to be depressed and in what sequence;
   c. specification means for activating said indicator means;
   d. measurement means for determining a response of said subject to the activation of said indicator means by said specification means;
   e. recording means for recording the response determined by said measurement means for said subject during an initial time period when said subject is free from any reflex impairment; and f. comparison means for comparing responses determined by said measurement means for said subject to said recorded response.

17. Apparatus for testing the reflexes of a subject comprising in combination:

a. a plurality of pressure sensing means each providing a signal when pressure is applied thereto by said subject;

b. indicator means associated with said plurality of pressure sensing means for specifying to said subject which of said plurality of pressure sensing means are to be depressed and in what sequence;

c. specification means for activating said indicator means;

d. measurement means for determining a response of said subject to the activation of said indicator means by said specification means;

e. comparison means for comparing responses determined by said measurement means for said subject to a predetermined quantity, said comparison means generating an enabling signal when responses determined by said measurement means have a predetermined relationship with said predetermined quantity; and f. delay means for inhibiting the generation of said enabling signal for a time penalty period when said comparison means determines that responses of said subject do not have said predetermined relationship with said predetermined quantity, said delay means increasing said time penalty period as a function of the number of times that responses of said subject do not have said predetermined relationship with said predetermined quantity.

* * * * *